[54] OPTO-ELECTRIC SENSING MEANS WITH PREDETERMINED DIRECTIONAL CHARACTERISTIC FOR ULTRASONIC WAVES

[75] Inventor: Walter Kaule, Cologne, Fed. Rep. of Germany

[73] Assignee: Krautkramer-Branson, Incorporated, Stratford, Conn.

[21] Appl. No.: 856,336

[22] Filed: Dec. 1, 1977

[30] Foreign Application Priority Data

Feb. 24, 1977 [DE] Fed. Rep. of Germany ....... 2707968

[51] Int. Cl.² ............................................. G01N 29/00
[52] U.S. Cl. ....................................... 73/643; 356/109
[58] Field of Search ................. 73/643, 655, 656, 657, 73/603; 356/109

[56] References Cited

U.S. PATENT DOCUMENTS 4,046,477    9/1977    Kaule .................... 356/109

Primary Examiner—James J. Gill
Attorney, Agent, or Firm—Ervin B. Steinberg; Philip J. Feig

[57] ABSTRACT

For sensing the presence of an ultrasonic wave propagated within a workpiece at the surface of such workpiece, the workpiece surface is illuminated with a laser beam and opto-electric means, such as an interferometer, are used to sense the minute workpiece surface deformation caused by the ultrasonic wave front. In order to sense the ultrasonic waves which are incident upon the workpiece surface at an oblique angle, the workpiece surface is illuminated in a pattern of equidistantly spaced strips. The spacing of the strips is determined by the angle of the ultrasonic wave and the wavelength of the ultrasonic wave. The resulting electrical signals are processed simultaneously or in sequence.

12 Claims, 2 Drawing Figures

OPTO-ELECTRIC SENSING MEANS WITH PREDETERMINED DIRECTIONAL CHARACTERISTIC FOR ULTRASONIC WAVES

FIELD OF THE INVENTION

This invention refers to a method and apparatus for providing a directional characteristic for a non-contacting optical receiver, e.g. a transit time interferometer, which is adapted to sense or measure the minute deformation of a workpiece surface caused by acoustic energy, particularly ultrasonic waves.

BACKGROUND OF THE INVENTION

When nondestructively testing solid materials for defects by ultrasonic energy, particularly a workpiece whose surface is not accessible or only accessible with difficulty, including a workpiece exhibiting a hot surface, it is necessary to receive the acoustic energy in a contact-free manner since liquid coupling means cannot be employed. The question of using gas as a coupling medium could arise, however, the very large difference of acoustic impedance between gas and a solid precludes the use of the latter medium. For ultrasonic testing sound waves are used which are propagated normal as well as at an oblique angle to the workpiece surface. The angle of sound propagation is determined largely by the orientation and location of the defect to be detected. It will be apparent that the directional characteristic of the receiver, that is, its angular sensitivity, must correspond to the angle of propagation of the acoustic wave.

Contact-free receiving means for sound waves having an incidence normal to a surface are known, and the deformation of the surface responsive to sonic energy can be measured, see "Werkstoffprüfung mit Ultraschall" (book) Krautkrämer, 3rd edition 1975, Springer-Verlag, Berlin/Heidelberg, page 169 and U.S. Pat. No. 4,046,477 of W. Kaule, dated Sept. 6, 1977, entitled "Interferometric Method and Apparatus for Sensing Surface Deformation of a Workpiece Subjected to Acoustic Energy".

However, no means have been developed heretofore to provide the opto-electrical receivers adapted to measure the minute surface deformation of a workpiece responsive to acoustic energy with a directional characteristic.

An important object of the present invention, therefore, is the provision of an optical receiving means used for contact-free reception of ultrasonic waves having a directional characteristic. The directional characteristic optimizes the reception of ultrasonic waves which are propagated in a workpiece at an angle deviating from perpendicular to the workpiece surface.

SUMMARY OF THE INVENTION

The above stated object is met by the present invention in that a portion of the workpiece surface, from which an ultrasonic wave having a given angle is to be received, is illuminated in a striped pattern, the strips forming the pattern being spaced equidistantly as determined by the angle of the ultrasonic wave relative to the workpiece surface.

For a better understanding of the present invention the following considerations may be helpful. When ultrasonic waves are transmitted from the interior of a workpiece to the surface thereof in such a manner that the sound beam is perpendicular to the workpiece surface, the workpiece surface portions will vibrate up and down in phase, provided that the surface is plane and the sound wave has a plane wave front. Such vibration can be measured, for instance with an interferometer, as a surface deformation, see Krautkramer and Kaule supra. However, when the sound wave is incident upon the workpiece surface at an oblique angle, not all of the surface portions move in phase. Only those portions are in phase which have a distance from one another meeting the condition:

$$d = (z \times \lambda)/\sin \alpha$$

These conditions are analogous to the diffraction of a plane wave at a grating. The only difference is that the effect is viewed from the opposite side.

The directions of maximum sensitivity are the same as those into which a wave is refracted by a grating.

As used in the equation above, $z$ is a natural number given by the refraction in accordance with the interference following Huygens' law ($z = 0$ for a diffracted beam of zero order, 1 for a diffracted beam of first order, i.e. the diffracted beam having the smallest angle); $\lambda$ being the wavelength of the sound and $\alpha$ being the angle between the perpendicular line and the diffracted beam, and $d$ being the center to center distance of the surface portions.

The receiving surface is defined as that workpiece surface portion which is illuminated and disposed within the view of the interferometer, that is, the surface portion at which sound waves are to be detected. The interferometer integrates the entire receiving surface and can process only in-phase vibration conditions. Such condition is present only when the sound waves are incident upon the workpiece surface along a perpendicular axis. For sound waves incident at an oblique angle there arise oppositely phased vibratory conditions within the receiving surface area and such conditions are zeroed when integrated. In order to evaluate the latter conditions it would be necessary to mask the receiving surface so severely as to evaluate only in-phase vibratory portions.

According to the relation:

$$d \times \sin \alpha = z \times \lambda \qquad (1)$$

such regions occur several times within the receiving area at the distance:

$$d = z \times \lambda/\sin \alpha \qquad (2)$$

Hence, it is required merely to illuminate the receiving surface with a grid pattern in such a manner that the illuminated portions coincide with the locations of in-phase vibratory states and, therefore, have a distance $d$ as determined by the above stated formulas (1) and (2) taking into account the wavelength of the sound wave and its angle relative to an axis perpendicular to the respective workpiece surface portion.

A method has been devised to receive in combination with an optical receiver under optimum conditions ultrasonic waves which are incident at a given angle. However, it should be noted that sound waves are received from two symmetric directions to the perpendicular axis, the waves corresponding to the diffraction beam of first order symmetric to the perpendicular.

When it is desired to preclude the receiver from being sensitive in two directions it is possible, in an alternative embodiment of the invention, to associate each light strip of the illuminated grid pattern with a separate and individual opto-electric means using known optical image arrangements. The electrical signals produced by the opto-electrical means are added after having passed through individual time delay circuits. The time delay is a function of the angle of the sound beam which is to be sensed by the receiver and the acoustic velocity. For the direction applicable to the first order of diffraction:

$$t = (d \times \sin \alpha)/c; \text{ hence } d \times \sin \alpha = c \times t$$

In the above equation $c$ equals the acoustic velocity of the sound wave to be received and $t$ is the sound transit time difference from illuminated strip to strip.

The above arrangement is responsive only to a single angle. The interference signals originating from the symmetrically disposed angular region are surpressed.

DETAILED DESCRIPTION OF THE INVENTION

Figure 1:
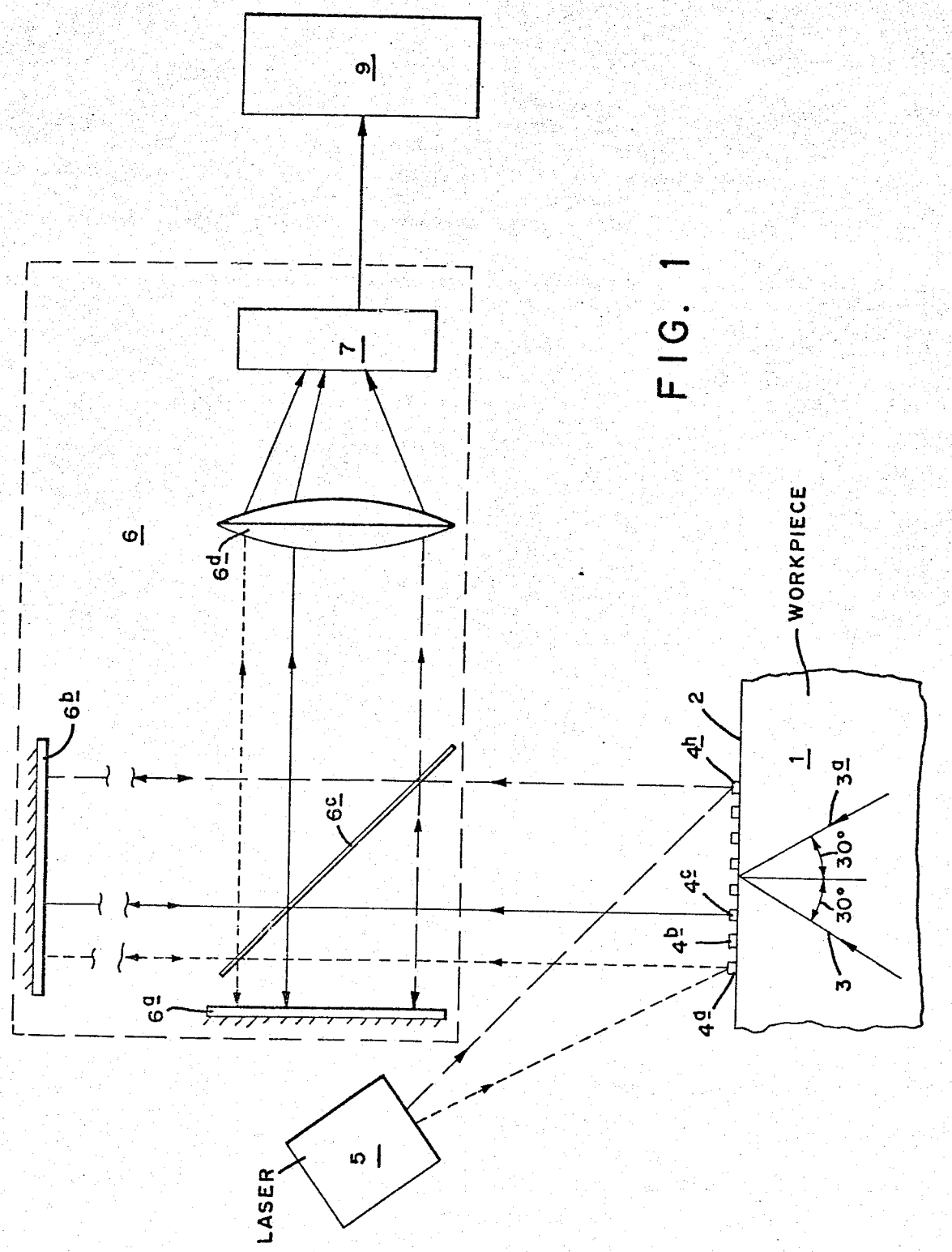
FIG. 1 is a schematic block diagram of a first embodiment of the present invention.

Referring now to the figures and FIG. 1 in particular, assuming that ultrasonic wave energy having a direction of propagation 3, which is 30° relative to the axis perpendicular to the workpiece surface, is to be sensed optically at the surface 2 of a workpiece 1, it will be necessary to illuminate the surface portion 2 and provide it also with a light grid pattern comprising a plurality of rectangular equidistantly spaced strips 4a, 4b, etc. For the sake of illustration, the strips 4a, 4b, etc. are shown raised above the workpiece surface 2. Typically, a grid mask of 0.2 mm copper foil is applied upon the desired surface portion, but alternatively a mask can be interposed in the path of the coherent light beam from the laser source 5 to the workpiece surface 2.

The following data shall apply for a typical example:

given: sound wavelength $\lambda = 1$ mm;
velocity of the acoustic wave energy $c = 6,000$ m/sec.

The center to center distance $d$ between the illuminated adjacent strips becomes then:

$$d = \lambda/\sin \alpha = 10^{-3}\text{m}/\sin 30° = 0.5 \times 10^{-3}\text{m} = 0.5 \text{ mm}.$$

The receiver 6 is a transit time opto-electrical interferometer of known type described in the patent to Kaule supra and comprises a mirror 6a, a mirror 6b, a beam splitter 6c, a lens 6d, and a photoelectric sensing means 7. The electrical output signal from the photoelectric sensing means 7 is transmitted to an evaluation circuit 9. The distance between the beam splitter 6c and the mirror 6b is the delay path for the reference beam portion as described in detail in Kaule supra. The arrangement shown in FIG. 1 senses sound waves from both indicated directions 3 and 3a. It should be noted that the signal received by the evaluation or processing circuit 9 is a sequence of signals responsive to the time spaced deformation of the surface portions 4a through 4h.

Figure 2:
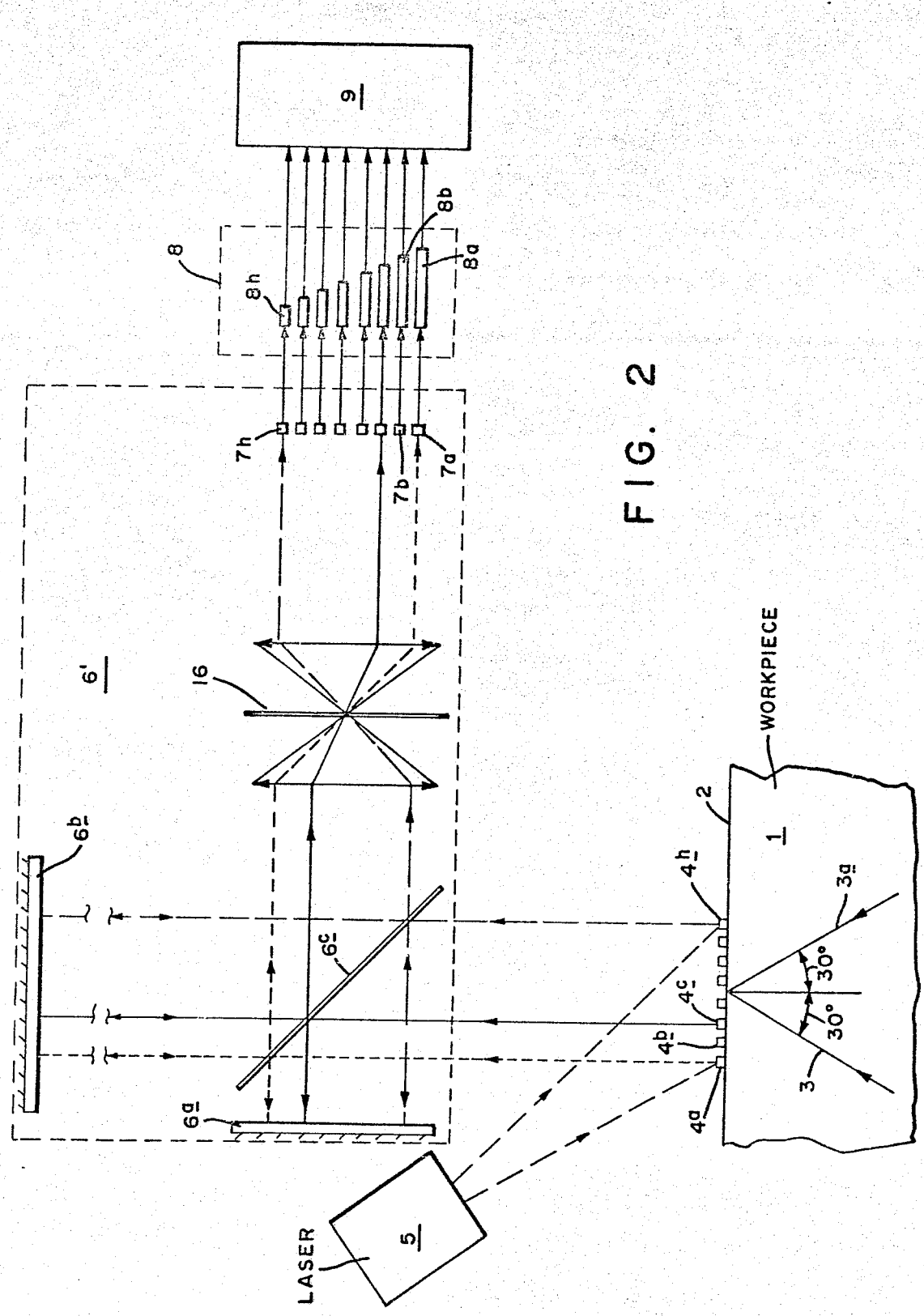
FIG. 2 is a schematic block diagram showing a modified embodiment.

In the event that the sound waves originating along direction 3a are not to be received, it will be necessary to modify the interferometer as shown in FIG. 2. The interferometer 6', FIG. 2, utilizes a directional filter 16 and a separate photoelectric sensing means 7a through 7h for each illuminated strip 4a through 4h along the workpiece surface.

Therefore, each photoelectric means, 7a through 7h, is responsive only to the acoustic energy induced surface deflection manifest at a respective surface portion, i.e. strip 4a through 4h. The output of each photocell 7a through 7h is coupled to a separate channel 8a through 8h of an electrical signal amplifier 8. Each channel, except channel 8h, includes, as necessary, an appropriate time delay as will be more evident from the following description.

The wave front of the sound beam 3 propagates along the workpiece surface and strikes initially the receiving surface with light grid at the strip 4a, causing the photocell 7a, which communicates with strip 4a, to become responsive to such deformation and to provide an electrical signal to amplifier channel 8a. This channel includes a time delay corresponding to $(n-1)t$ wherein $n$ equals the quantity of strips. For the condition $d = 0.5$ mm, $\sin \alpha = 0.5$, $c = 6,000$ m/sec, and $n = 8$, the value $t$ becomes 41.67 nsec. Thus, $7 \times 41.67$ nsec = 291.69 nsec. The electrical signal derived from the photocell 7a, therefore, is is provided to the processing circuit 9 delayed by 291.69 nanoseconds. At the time 41.67 nsec the wave front arrives at the strip 4b, rendering the photocell 7b associated with strip 4b responsive to surface deformation. The photocell 7b provides a signal to amplifier channel 8b which signal, in turn, is time delayed by $6 \times 41.67$ nsec, or 250.02 nanoseconds.

This process is continued until the last strip 4h is deflected causing a signal at photocell 7h which provides a non-delayed signal to the processing circuit 9. As a result, the processing circuit receives all of the signals from channels 8a through 8h simultaneously, causing a summing of the electrical signals. For wave fronts having angles deviating from 30°, the electrical delays in the amplifier channels 8a through 8h do not coincide with the appearance of the wave fronts at the strips, hence the electrical signals are not received simultaneously at the circuit 9 and, therefore, are not added. For other conditions the time delays associated with the amplifier channels must be selected correspondingly as described in connection with the example stated above.

The laser beam provided by the laser 5 must be of relatively low energy to prevent the generation of acoustic energy at the workpiece surface. The grid mask can be disposed on the workpiece by adhesion or if a ferromagnetic workpiece is used magnetic holders are possible. As indicated for optical projection and thereby desiring a truly contact-free reception, the mask in the form of a metal grid evaporated on glass, is interposed in the beam from laser 5 to the workpiece. In a preferred embodiment the width of the illuminated strips 4a through 4h is selected to be from 0.1 to 0.5 the grid constant, i.e. value $d$.

In an alternative embodiment the individual photoelectric detectors can be interrogated by a series-to-parallel shift register and the respective values added in a summing circuit. In the latter case, the interrogation by the shift register and the laser scanning is synchronized by suitable timing means.

It will be apparent that the above described method and apparatus provide in an advantageous manner an arrangement for the contact-free sensing of ultrasonic waves at a workpiece surface when the waves have an angle of incidence deviating from normal to the workpiece surface.

What is claimed is:

1. The method for determining by opto-electric sensing means the presence of ultrasonic waves at a workpiece surface by sensing the ultrasonic wave responsive localized workpiece surface deformation comprising:
illuminating the surface portion of the workpiece at which ultrasonic waves are to be sensed with coherent light in a pattern to cause a plurality of equidistantly spaced illuminated strips;
disposing opto-electric sensing means for receiving reflected light from said strips;
sensing the changes in illumination manifest at said opto-electric means as the illuminated surface strips are deformed responsive to ultrasonic waves arriving at said surface portion and providing corresponding electrical output signals, and
processing said output signals;
the distance between said strips being selected substantially in accordance with the equation $$d = \lambda/\sin \alpha$$

wherein $d$ is the distance between the center of adjacent strips, $\lambda$ is the wavelength of the ultrasonic wave, and $\alpha$ the angle of the ultrasonic wave relative to an axis intersecting the workpiece surface portion at a normal angle.

2. The method for determining by opto-electric sensing means the presence of ultrasonic waves at a workpiece surface as set forth in claim 1, said changes in illumination providing a sequence of electrical output signals as an ultrasonic wave propagates along the workpiece surface and sequentially deforms the area defined by a respective strip, and processing said respective output signals in received sequence.

3. The method for determining by opto-electric sensing means the presence of ultrasonic waves at a workpiece surface as set forth in claim 1, and providing a plurality of opto-electric sensing means, disposing each respective sensing means to be responsive to the light from a respective strip, thereby obtaining a sequence of respective electrical output signals from said plurality of sensing means as an ultrasonic wave propagates along the workpiece surface and sequentially deforms the area defined by a respective strip, and selectively delaying said respective output signals to cause them to be available substantially simultaneously for processing.

4. Apparatus for sensing by optical receiving means the deformation of a workpiece surface arising from an ultrasonic wave propagated and being incident upon such workpiece surface comprising:
laser means disposed for transmitting a beam of light toward the workpiece surface portion at which such deformation is to be sensed;
means disposed in the light path of said beam for causing a pattern of equidistantly spaced illuminated strips on said surface portion;
opto-electrical sensing means disposed for receiving reflected light from said strips and providing respective electrical output signals responsive to said strips being deformed by an ultrasonic wave;
a processing circuit coupled for receiving said electrical output signals, and
the distance between said strips being selected substantially in accordance with the equation $$d = \lambda/\sin \alpha$$

wherein $d$ is the distance between the center of adjacent strips, $\lambda$ the wavelength of the ultrasonic wave, and $\alpha$ the angle of the ultrasonic wave relative to an axis intersecting the surface portion at a normal angle.

5. Apparatus for sensing by optical receiving means the deformation of a workpiece surface as set forth in claim 4, said optical electrical sensing means comprising a transit time interferometer.

6. Apparatus for sensing by optical receiving means the deformation of a workpiece surface as set forth in claim 4, and delay means coupled in circuit with said sensing means for selectively delaying said respective electrical output signals to cause said respective output signals to be available substantially simultaneously as an input signal at said processing circuit.

7. Apparatus for sensing by optical receiving means the deformation of a workpiece surface as set forth in claim 4, said opto-electrical sensing means including a plurality of photoelectric means, a respective photoelectric means being responsive to the deformation of a respective strip, and circuit means coupled selectively between said plurality of photoelectric means and said processing circuit for causing said respective output signals to be available substantially simultaneously at said processing circuit.

8. Apparatus for sensing by optical receiving means the deformation of a workpiece surface as set forth in claim 7, said circuit means comprising time delay means.

9. Apparatus for sensing by optical receiving means the deformation of a workpiece surface as set forth in claim 7, said circuit means comprising a shift register.

10. Apparatus for sensing by optical receiving means the deformation of a workpiece surface as set forth in claim 7, said time delay means comprising electrical signal delay means.

11. Apparatus for sensing by optical receiving means the deformation of a workpiece surface as set forth in claim 7, said processing circuit including summing means.

12. Apparatus for sensing by optical receiving means the deformation of a workpiece surface as set forth in claim 4, the width of a respective strip being from 0.1 to 0.5 the value of $d$.

* * * * *